(12) United States Patent
Konakahara (10) Patent No.: US 7,707,647 B2
(45) Date of Patent: Apr. 27, 2010

(54) PROBE USED FOR SURFACE ENHANCED VIBRATIONAL SPECTROSCOPIC ANALYSIS AND METHOD OF MANUFACTURING THE SAME

(75) Inventor: Kaoru Konakahara, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 202 days.

(21) Appl. No.: 12/110,768

(22) Filed: Apr. 28, 2008

(65) Prior Publication Data

US 2008/0286563 A1 Nov. 20, 2008

(30) Foreign Application Priority Data

May 14, 2007 (JP) .............................. 2007-128271

(51) Int. Cl.
*G01Q 60/22* (2010.01)

(52) U.S. Cl. .................. 850/32; 977/862; 977/875; 977/879; 428/328; 356/301; 427/180; 427/203

(58) Field of Classification Search .................. 850/32; 977/862, 875, 879; 428/328; 356/301; 427/180, 427/203
See application file for complete search history.

(56) References Cited

U.S. PATENT DOCUMENTS

| | | | |
|---|---|---|---|
| 7,241,987 B2 * | 7/2007 | Saito et al. .................. | 250/234 |
| 7,288,419 B2 | 10/2007 | Naya | |
| 7,572,300 B2 * | 8/2009 | Cohen et al. .................. | 850/58 |

| | | | |
|---|---|---|---|
| 2005/0105085 A1 | 5/2005 | Naya | |

FOREIGN PATENT DOCUMENTS

| | | | |
|---|---|---|---|
| JP | 2005-172569 | | 6/2005 |
| JP | 2006194715 A | * | 7/2006 |

OTHER PUBLICATIONS

M. Fleischmann et al., "Raman Spectra of Pyridine Adsorbed at a Silver Electrode", Chemical Physics Letters, 1974, vol. 26, No. 2, pp. 163-166.

Y. Kobayashi et al., "Surface-Enhanced Resonance Raman Scattering Spectra of Meso-Substituted Porphines In Layered Structures Having CaF2/Porphine/Ag and CaF2/Ag/Porphine Configurations", J. Phys. Chem., 1985, vol. 89, No. 24, pp. 5174-5178.

S. Hayashi et al., "SERS Activity of Gas-evaporated Silver Particles", Solid State Communications, 1985, vol. 55, No. 12, pp. 1085-1088.

(Continued)

*Primary Examiner*—Jack I Berman
(74) *Attorney, Agent, or Firm*—Fitzpatrick, Cella, Harper & Scinto (57) ABSTRACT

Provided are a probe for surface enhanced vibrational spectroscopic analysis which has excellent detection sensitivity to laser light having an intensity level at which a sample is not damaged and which has a long life, and a method of manufacturing the probe. The probe for surface enhanced vibrational spectroscopic analysis is formed on a cantilever. A plurality of metal fine particles are dispersed in the probe. The plurality of metal fine particles are exposed on the surface of the probe.

12 Claims, 4 Drawing Sheets

OTHER PUBLICATIONS

M. Futamata et al., "Local Electric Field and Scattering Cross Section of Ag Nanoparticles under Surface Plasmon Resonance by Finite Difference Time Domain Method", J. Phys. Chem. B, 2003, vol. 107, pp. 7607-7617.

N. Hayazawa et al., "Near-field Raman scattering enhanced by a metallized tip", Chemical Physics Letters, 2001, 335, pp. 369-374.

A. Chandra et al., "Monodisperse nanoparticles via metal induced crystallization", Journal of Applied Physics, 2004, vol. 96, No. 11, pp. 6776-6781.

* cited by examiner

PROBE USED FOR SURFACE ENHANCED VIBRATIONAL SPECTROSCOPIC ANALYSIS AND METHOD OF MANUFACTURING THE SAME

BACKGROUND OF THE INVENTION

1. Field of the Invention

The present invention relates to a probe used for surface enhanced vibrational spectroscopic analysis and a method of manufacturing the probe.

2. Description of the Related Art

When a sample is irradiated with laser light, Raman scattered light, which is different in frequency from original incident light, is emitted from the sample together with Rayleigh scattered light, which is equal in frequency to the original incident light. The Raman spectroscopic analysis method of analyzing the Raman scattered light is effective to determine a molecular structure or a bonding state of crystals.

However, there is a case where a sample such as an organic substance is sensitive to damage by laser light, so it is necessary to measure the sample at minimum laser intensity. Because the intensity of the Raman scattered light is extremely weak, when the sample is a thin film or when a measurement area is very small, it may be difficult to obtain the Raman spectrum. Therefore, there is required a technique for detecting the Raman scattered light whose intensity is extremely weak at high sensitivity even when the sample is irradiated with laser light at an intensity level at which the sample is not damaged.

An example of the technique includes surface enhanced Raman scattering (SERS) (see Chem. Phys. Lett., Vol. 126, p.163 (1974)). The SERS is a phenomenon in which the intensity of Raman scattered light from a sample of a monomolecular layer or a several-molecular layer which is deposited on a substrate on which a metal film made of a noble metal such as silver, gold, or copper (island-like film or fine particle film) is formed becomes $10^2$ to $10^6$ times larger than the intensity of Raman scattered light from a sample deposited on a substrate on which the metal film is not formed. It is also necessary to make the surface of the metal film rough. For example, a film which contains Si particles, Ag particles, or $CaF_2$ having a μm size is formed as a base film. When the metal film is formed on the base film, the roughness of the surface of the metal film increases, so the SERS is observed at higher sensitivity (see J. Phys. Chem. 1985, 89, 5174-5178, and Solid State Communications, Vol. 55, No. 12, pp. 1085-1088, 1985). Even when the metal film is deposited on the surface of the sample, the SERS phenomenon is observed.

The same is expected even in the case of an infrared spectroscopic analysis method. When the sample is irradiated with infrared light, an infrared light having a frequency peculiar to the sample is absorbed thereinto. Information with respect to molecular structure or environments of the molecules is obtained based on a frequency at an absorption position.

In recent years, a scanning probe microscope, a near-field microscope, and an atomic force microscope have been under development. Therefore, the structure of each metal nano fine particle can be measured in the nanoscale and simultaneously the interparticle distance can be controlled to detect Raman scattered light only from a specific particle to which an extremely small amount of molecules are absorbed. For example, according to J. Phys. Chem. B. 2003, 107, 7607-7617, it has been reported that when a metal nano structure which produces sufficient SERS is irradiated with laser light, the local electric field intensity on the surface of the nano structure is obtained by numeral calculation, thereby finding the metal nano structure which provides a very large enhanced intensity. When a local electric field intensity on an isolated spherical or elliptical metal nano particle is calculated, only an SERS enhanced intensity of $10^4$ to $10^5$ is obtained. In contrast to this, an enhanced intensity of $10^{10}$ or more, which is equivalent to the monomolecular sensitivity, is obtained on a bonding area between spherical or elliptical nano particles at an optimum wavelength without depending on the particle size. Therefore, it is reported that the very large enhanced intensity of the monomolecular sensitivity is obtained on the aggregation of the metal nano particles and the bonding area therebetween.

A metal is filled into fine pores and exposed to shorten the distance between respective exposed metal fine particles to several nm. A sample to be analyzed is attached to the surfaces of the exposed metal fine particles and irradiated with laser light. Therefore, surface enhanced Raman scattering measurement using an electromagnetic field generated between the metal fine particles to improve the sensitivity can be performed (see U.S. Publication 2005/0108085).

When a tip portion of a near-field microscope probe such as a probe in which a metal film whose thickness is several nm to several tens nm is formed on the surface thereof is irradiated with light, a locally strong electromagnetic field generates near the tip portion. When the tip portion of the probe is irradiated with light while the tip portion of the probe is brought close to or into contact with a measurement sample, the surface enhanced Raman scattering measurement is performed at high sensitivity. Such a phenomenon is called tip enhanced Raman scattering (TERS) (see Chemical Physics Letters, 335, 369-374, 2001). According to this report, for example, when the probe coated with the metal film is brought close to or into contact with the measurement sample, a sufficient intensity is obtained because of SERS.

In particular, in order to obtain a sufficient SERS intensity using metal nano structures such as particles, it is necessary to arrange the metal nano structures at an interval of approximately 0 nm to several nm. According to the conventional tip enhanced Raman scattering technique, the film thickness of the metal film applied as a coating of the tip portion of the probe can be controlled. However, it is difficult to control a shape of the metal film (to obtain island-like film or particle-like film). In addition, it is difficult to control the interval between metal fine particles.

Molecules of the measurement sample may be absorbed to the metal film coating the tip portion of the probe every time the probe is brought into contact with the measurement sample. Therefore, there is also such a problem that the probe is frequently discarded.

SUMMARY OF THE INVENTION

The present invention has been made in view of the two problems described above. An object of the present invention is to provide a probe to be used for surface enhanced vibrational spectroscopic analysis with which detection sensitivity can be improved as desired and a long life can be realized even in the case where a sample is irradiated with laser light at an intensity level at which the sample is not damaged, and a method of manufacturing the probe.

To solve these problems, according to the present invention, there is provided a probe used for surface enhanced vibrational spectroscopic analysis, the probe being formed on a cantilever, the probe including a plurality of metal fine particles dispersed therein, the plurality of the metal fine particles being exposed on a surface of the probe.

Further, according to the present invention, there is provided a method of manufacturing a probe for use in surface enhanced vibrational spectroscopic analysis, including forming a projected portion on a cantilever; forming a Si film including a metal fine particle layer so as to be in contact with the projected portion; heating the Si film including the metal fine particle layer to disperse metal fine particles in the Si film; and forming the probe by processing the Si film, in which a plurality of the metal fine particles are exposed on a surface of the probe by the step of forming the probe.

According to the present invention, it is possible to improve the detection sensitivity of the probe to be used for surface enhanced Raman scattering spectroscopic analysis as desired. The long life of the probe for surface enhanced vibrational spectroscopic analysis can be realized. It is possible to provide the method of manufacturing the probe for surface enhanced vibrational spectroscopic analysis in which the detection sensitivity can be improved as desired and the long life can be realized.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIGS. 1A and 1B are schematic views illustrating probes for surface enhanced vibrational spectroscopic analysis according to the present invention, in which FIG. 1A illustrates a probe in which metal fine particles are exposed on a surface thereof.

FIGS. 2A, 2B, 2C and 2D illustrate the steps of one embodiment of a method of manufacturing the probe in which the metal fine particles are dispersed, according to the present invention, in which FIG. 2A illustrates a step of forming a cantilever; FIG. 2B illustrates a step of forming an alternately layered film; FIG. 2C illustrates a heat treatment step; and FIG. 2D illustrates a step of forming the probe.

FIGS. 3A and 3B illustrate a step of forming the metal film by plating, in which FIG. 3A illustrates a state before plating; and FIG. 3B illustrates a state after plating.

FIGS. 4A and 4B illustrates a step of etching a surface of the probe, in which FIG. 4A illustrates a state before etching; and FIG. 4B illustrates a state after etching.

DESCRIPTION OF THE EMBODIMENTS

Preferred embodiments of the present invention will now be described in detail in accordance with the accompanying drawings.

Figure 1A:
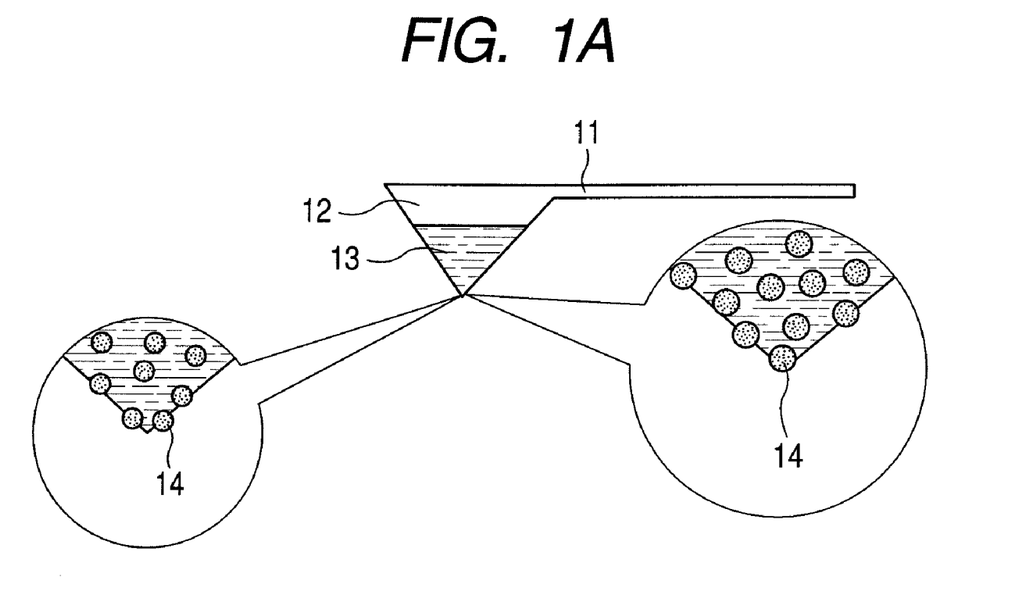
Figure 1B:
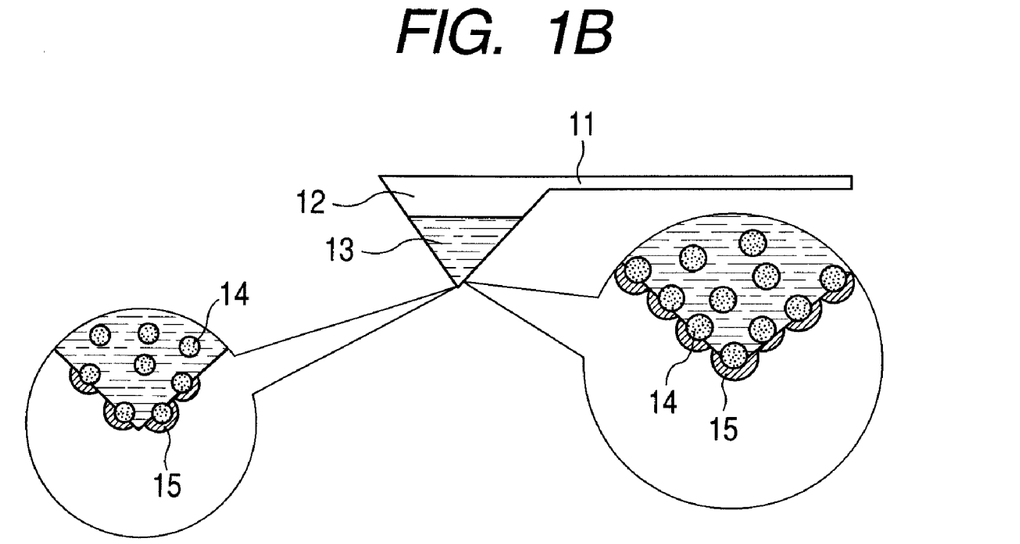
FIG. 1B illustrates a probe in which metal fine particles to which metal films are formed are exposed on a surface of the probe; an enlarged schematic view located on the left side of each of FIGS. 1A and 1B illustrates a tip portion of the probe in which a plurality of metal fine particles are exposed; and an enlarged schematic view located on the right side of each of FIGS. 1A and 1B illustrates a tip portion of the probe in which a single metal fine particle is exposed.

First, a probe for surface enhanced vibrational spectroscopic analysis according to the present invention will be described (FIGS. 1A and 1B).

FIG. 1A illustrates a probe according to the present invention. A probe 13 is formed on a projected portion 12 located at the tip end of a cantilever 11. The probe 13 includes a large number of metal fine particles 14 dispersed thereinto. The probe 13 is of a pyramid structure made of a Si material. The large number of metal fine particles 14 are exposed on the surface of the probe 13.

FIG. 1B illustrates another probe according to the present invention. A probe 13 is formed on the projected portion 12 located at the tip end of the cantilever 11. The probe 13 includes the large number of metal fine particles 14 dispersed thereinto. The probe 13 is of a pyramid structure made of a Si material. Metal films 15 are formed so as to cover exposed portions of the metal fine particles 14 exposed on the surface of the probe 13.

The probe 13 is desirably of the pyramid structure which includes the metal fine particles 14 dispersed thereinto and is made of the Si material. The pyramid structure may be a conical structure or a polygonal structure.

The height of the probe 13 (distance between the surface of the projected portion 12 located at the tip end of the cantilever and the tip portion of the probe 13 in the longitudinal direction) is not particularly limited. The height can be set in a range of 100 nm to 100 μm. The length of the side of each bottom of the probe 13 is also not limited. The length can be set in a range of 100 nm to 100 μm. The tip portion shape of the probe 13 may be a hemispherical shape whose radius of curvature is 10 nm to 100 nm or a square planar shape whose each side length is 10 nm to 100 nm. In particular, a hemispherical shape whose radius of curvature is 10 nm to 50 nm is desirable.

The material of the metal fine particles 14 is desirably any one of Au, Ag, Pd, and Pt and the particle size thereof is desirably 1 nm to 30 nm. This is because an SERS phenomenon relatively easily occurs in the particle size range. The interspace distance between the metal fine particles 14 dispersed into the probe 13 and the interspace distance between the exposed metal fine particles is desirably 0 nm to 100 nm, particularly desirably 0 nm to 50 nm. This is because the SERS phenomenon relatively easily occurs in this interspace distance range. The metal fine particles 14 may be a mixture of Si and metal, such as $M_xSi_{1-x}$ ($0 \leq x \leq 1$, M is any one of Au, Ag, Pd, and Pt). Note that the "interspace distance" means the shortest distance between the particle surfaces of two adjacent metal fine particles. The case where the interspace distance is '0' indicates a state in which the metal fine particles are in contact with one another.

The metal films 15 are desirably made of any one of Au, Ag, Pt, and Pd. The film thickness of the metal films 15 is desirably 1 nm to 50 nm.

Next, a method of manufacturing the probe for surface enhanced vibrational spectroscopic analysis according to the present invention will be described.

The probe for surface enhanced vibrational spectroscopic analysis which is used to perform vibrational spectroscopic analysis on a sample, according to the present invention will be manufactured by at least the following process. The process includes a step of forming a layered film 21 on the projected portion 12 located at the tip end of the cantilever 11, a step of converting the layered film 21 to a metal fine particle dispersed film 24, and a step of forming the probe 13 from the metal fine particle dispersed film 24.

A method of manufacturing the probe for surface enhanced vibrational spectroscopic analysis as illustrated in FIG. 1A will be described in detail below.

An example of the method of manufacturing the probe for surface enhanced vibrational spectroscopic analysis in the following case will be described in the order of Step (a) to Step (d) below (FIGS. 2A to 2D).

Figure 2A:
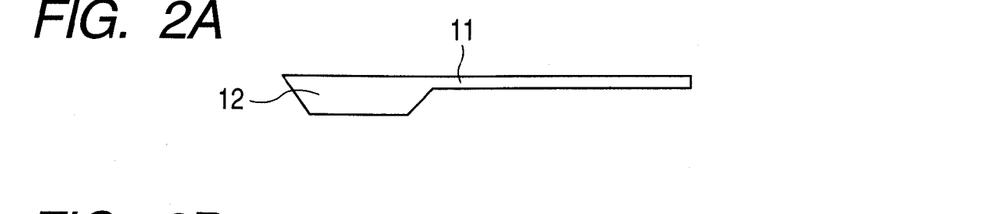

(a) Step of Forming Projected Portion 12 Located at Tip End of Cantilever 11 (FIG. 2A)

An example of a processing method which can be used for the step of forming the projected portion 12 located at the tip end of the cantilever 11 includes a microprocessing technique such as plasma etching or sputter etching. In the present invention, for example, the cross sectional surface of the projected portion 12 of a pyramid structure located at the tip end of the cantilever 11 of a Si material normally available on the market for use in a scanning probe microscope is partially processed or etched using a focused ion beam from a liquid metal ion source such as a Ga source. The surface shape of the projected portion 12 is desirably a square planar shape. The length of each side of the square planar shape can be set in a range of 100 nm to 100 μm. For example, the projected portion 12 to be formed has a square planar surface whose each side length is 10 μm.

Figure 2B:
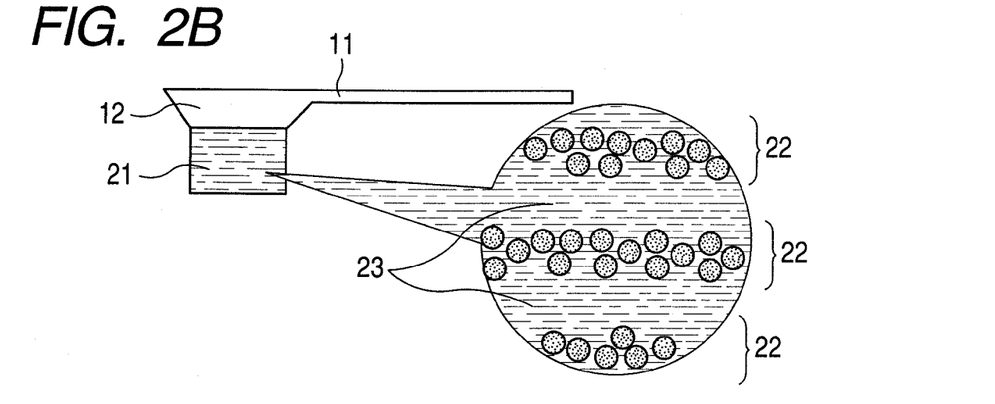

(b) Step of Forming Layered Film 21 (FIG. 2B)

Examples of a method of forming the layered film 21 include a sol-gel method, a vapor deposition method, and a sputtering method. In the present invention, the sputtering method is employed.

A metal fine particle layer 22 and a Si layer 23, each of which has a desirable film thickness, can be alternately formed. The film thickness of the Si layer 23 is desirably equal to or smaller than the film thickness of the metal fine particle layer 22. For example, the metal fine particle layer 22 having a film thickness of 20 nm and the Si layer 23 having a film thickness of 30 nm are alternately layered on the projected portion 12 located at the tip end of the cantilever 11 until the layered film 21 whose film thickness is approximately 10 μm is obtained.

Any one of Au, Ag, Pd, and Pt may be used as a material of the metal fine particle layer 22. A mixture of Si and metal, such as $M_xSi_{1-x}(0 \leqq X \leqq 1$, M is any one of Au, Ag, Pd, and Pt) may also be used as the material. In the present invention, for example, the metal fine particle layer 22 made of $Au_{0.4}Si_{0.6}$ and the Si layer 23 may be alternately formed by a sputtering method using an Au target and a Si target.

With respect to the formation conditions of the layered film, an inert gas such as Ar or He may be used as an atmospheric gas and the alternate layer formation may be performed in high vacuum. In the present invention, the pressure of the inert gas is desirably 1 mTorr to 100 mTorr. The layer formation is desirably performed at a deposition rate of 0.3 angstroms/second to 1.1 angstroms/second.

In FIG. 2B, the metal fine particle layer 22 includes the metal fine particles 14 and Si. In other words, when the film thickness of the metal film layered on the Si layer 23 is thin, metals aggregate into the metal fine particles 14. After that, the Si thin film is formed on the metal fine particles 14. At this time, Si is deposited in an interspace between the metal fine particles 14.

Figure 2C:
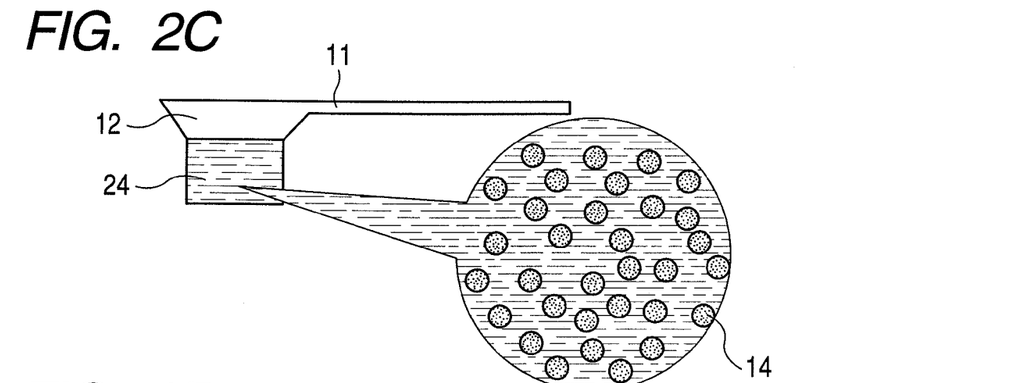

(c) Step of Forming Metal Fine Particle Dispersed Film 24 (FIG. 2C)

In order to convert the layered film 21 formed in Step (b) to the metal fine particle dispersed film 24, a heat treatment step is performed. The heat treatment step is desirably performed in vacuum or in an inert gas atmosphere such as an Ar atmosphere or a He atmosphere. In particular, it is desirable to perform the heat treatment step in an inert gas atmosphere at an atmospheric pressure. The heat treatment temperature and the heat treatment time may be controlled as desired. In particular, it is desirable to select a heat treatment condition which is suitable to sufficiently disperse the metal fine particles 14 based on a film thickness ratio between the Si layer 23 and the metal fine particle layer 22, thereby performing the heat treatment.

In the present invention, when the metal fine particle layer 22 made of $Au_{0.4}Si_{0.6}$ and the Si layer 23 are alternately formed, the heat treatment temperature is desirably 200° C. to 300° C. and the heat treatment time is desirably 30 minutes to 2 hours (see Journal of Applied Physics, Vol. 96, No. 11, 2004, p. 6776).

Figure 2D:
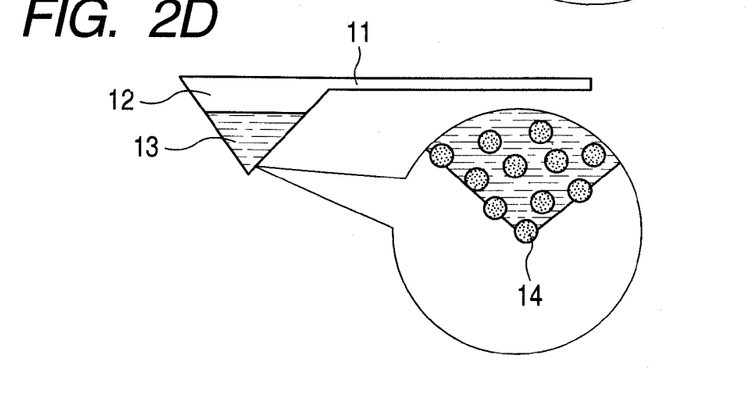

(d) Step of Forming Probe 13 (FIG. 2D)

A microprocessing technique such as plasma etching or sputter etching is used as in Step (a). The probe 13 having a pyramid structure or a polygonal structure is desirably formed from the metal fine particle dispersed film 24 obtained by the formation and the heat treatment in Step (b) and Step (c). The probe 13 having a desirable bottom side length and a desirable height is desirably formed.

For example, the probe 13 having the pyramid structure is formed from the metal fine particle dispersed film 24 by focused ion beam etching. The probe 13 has a bottom side length of 10 μm and a height of approximately 10 μm. The tip portion shape of the probe 13 is a hemispherical shape whose radius of curvature is 30 nm. The probe 13 is desirably provided such that a single metal fine particle (right side of FIG. 1A) 14 or a plurality of metal fine particles (left side of FIG. 1B) 14 are exposed in the tip portion thereof.

When the metal fine particles 14 are to be further exposed, for example, the following desirable etching is performed. A solution for slightly dissolving the Si material of the surface of the probe 13 is prepared and the cantilever 11 with the probe 13 is immersed in the solution for several minutes. The solution desirably has an acid of pH 2 to pH 6 or an alkali of pH 10 to pH 14. A desirable solution is a strong acid solution such as a phosphoric acid solution, a sulfuric acid solution, a hydrochloric acid solution and a chromic acid solution, or a strong alkali solution such as a sodium hydroxide solution and ammonia water. However, the present invention is not particularly limited to these types of acid and alkali.

Next, a method of manufacturing the probe for surface enhanced vibrational spectroscopic analysis as illustrated in FIG. 1B will be described in detail below.

A method of manufacturing the probe for surface enhanced vibrational spectroscopic analysis in the case where plating is used for a step of forming the metal film 15 on the surfaces of the exposed metal fine particles 14 will be described. One of electrolytic plating and nonelectrolytic plating can be employed. In this method, the case where electrolytic plating is used will be described in detail (FIGS. 3A and 3B).

Figure 3A:
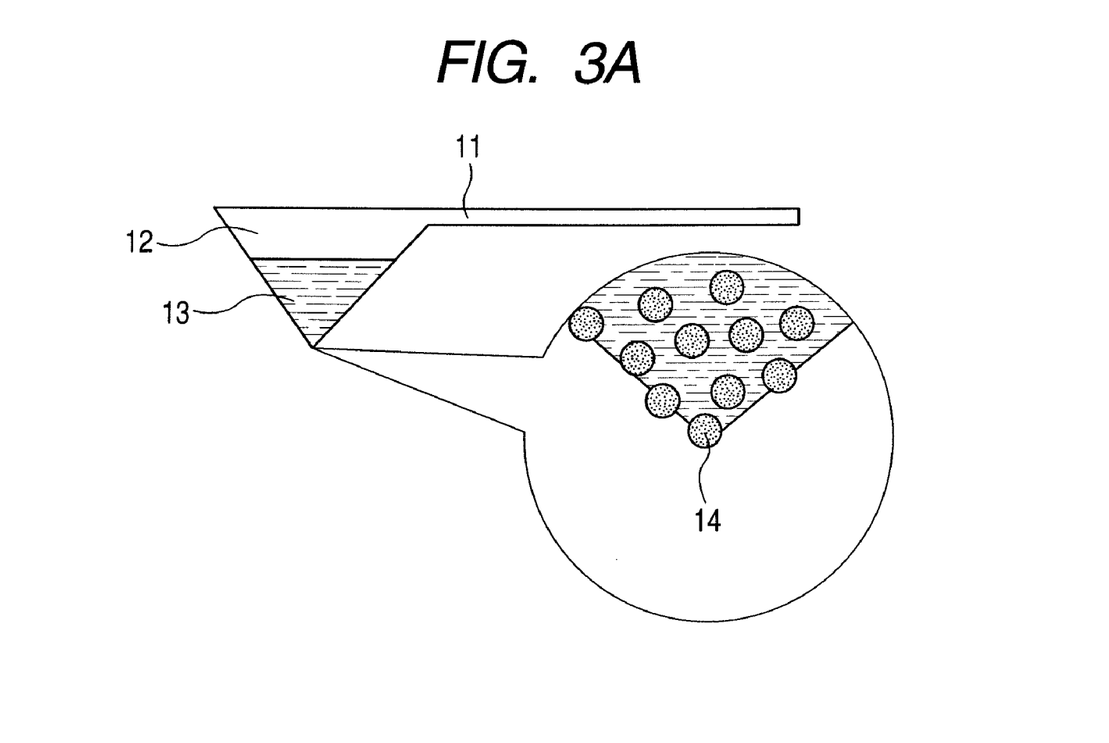
Figure 3B:
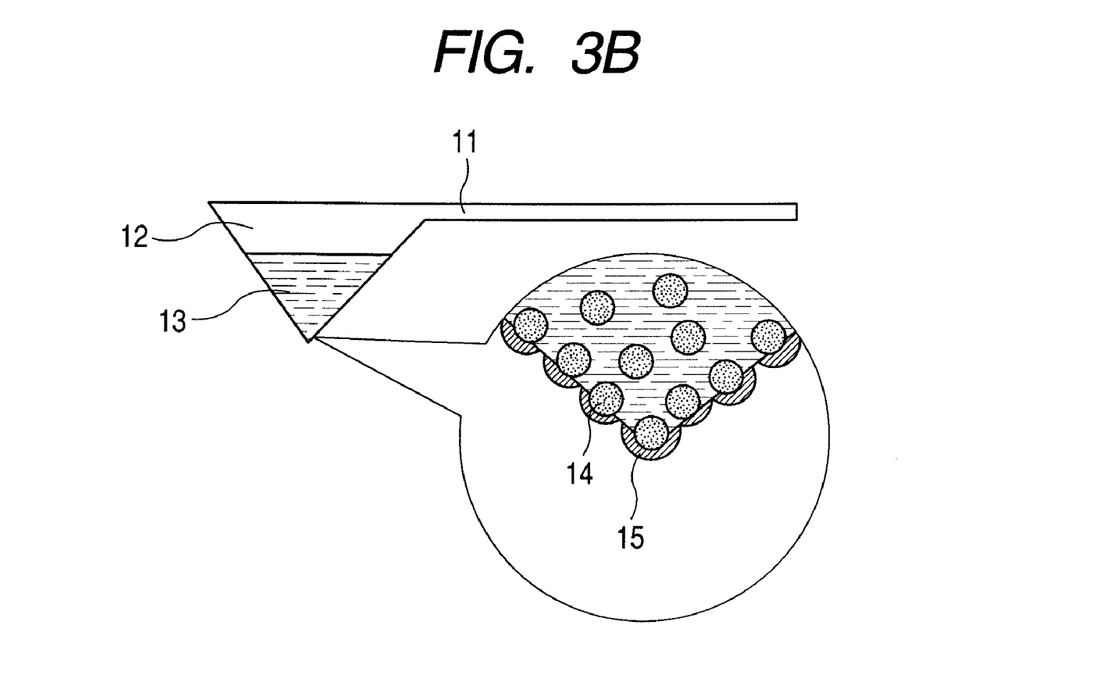

As illustrated in FIG. 1A, the probe for surface enhanced vibrational spectroscopic analysis in which the metal fine particles 14 are exposed on the surface of the tip portion of the probe 13 is manufactured (FIG. 3A). Subsequently, an electrode substrate is placed in a plating bath (electrolytic plating bath) including a salt containing metal to be precipitated, that is, a metal salt. The electrode substrate includes the cantilever 11 with the probe 13 in which the metal fine particles 14 are exposed and an anode made of Pt or Ag. When a potential or current is applied under this condition, the metal film 15 can be formed on the exposed portions of the metal fine particles 14 exposed on the surface of the tip portion of the probe 13 (FIG. 3B).

Conditions for forming the metal film 15 by electrolytic plating include a combination of component types in the plating bath including at least the metal salt, respective concentrations, a plating bath temperature, an agitation speed, pH adjustment, a plating time, an applied current value, and a type of an anode material. When the conditions are controlled, the metal film 15 can be formed at a desirable film thickness.

The interspace distance between the metal fine particles 14 for which the metal film 15 is formed on the surfaces thereof is desirably 0 nm to 50 nm, more desirably 0 nm to 3 nm. In the present invention, a desirable material of the metal films 15 formed by electrolytic plating is a noble metal such as Au, Ag, Pd, or Pt.

Next, a vibrational spectroscopic analysis method using the probe for surface enhanced vibrational spectroscopic analysis according to the present invention will be described.

The probe for surface enhanced vibrational spectroscopic analysis according to the present invention is a probe for surface enhanced Raman spectroscopic analysis and will be described in detail below.

In the Raman spectroscopic analysis method using the probe 13, a measurement sample of a layer of a single molecule or several or more molecules is deposited on the surface of a substrate with a metal film or the surface of a glass substrate by a spin coating method or a vapor deposition method. Then, the probe coated with the metal film is brought close to or into contact with the substrate. In general, with such a state, the tip portion of the probe is irradiated with laser light to perform the Raman spectroscopic analysis. For example, an organic solution is desirably dropped on the glass substrate and dried, and then the tip portion of the probe 13 is desirably brought close to or into contact with the glass substrate to perform the Raman spectroscopic analysis.

An organic substance, that is, a dissolved substance, of the organic solution is desirably an organic substance which includes a functional group such as a thiol group or an amino group and has surface enhanced Raman activity. Deionized water or an organic solvent such as ethanol or ethylene glycol is desirably used as a solvent. The concentration in the organic solution is desirably 0.001 mmol/L to 1 mol/L, particularly desirably 0.001 mmol/L to 1 mmol/L.

For example, in the case of a copper phthalocyanine (CuPc) aqueous solution, a 0.1 mmol/L of the CuPc aqueous solution (25° C. room temperature) is prepared, and then the aqueous solution is dropped on the glass substrate and dried.

According to the probe for surface enhanced vibrational spectroscopic analysis of the present invention, the single metal fine particle 14 or the plurality of metal fine particles 14 are exposed in the tip portion of the probe 13. The probe 13 is brought close to or into contact with the substrate to which the organic molecules are absorbed. Therefore, surface enhanced Raman scattered light can be measured at high sensitivity by a great electromagnetic field generated near the metal fine particles 14 or in an interspace region (0 nm to 100 nm) between the metal fine particles 14. Unlike the case of the single metal fine particle 14, the detection sensitivity in the case of the plurality of metal fine particles 14 is improved with increasing number of interspace regions between the metal fine particles 14.

When the metal fine particles 14 for which the metal film 15 is formed on the surfaces thereof are used, the interspace distance between the metal fine particles 14 is further shortened (0 nm to 10 nm), with the result that the intensity of an electromagnetic field generated in the interspace is further increased to improve the detection sensitivity.

Next, an extension of life of the probe for surface enhanced vibrational spectroscopic analysis according to the present invention will be described.

Figure 4A:
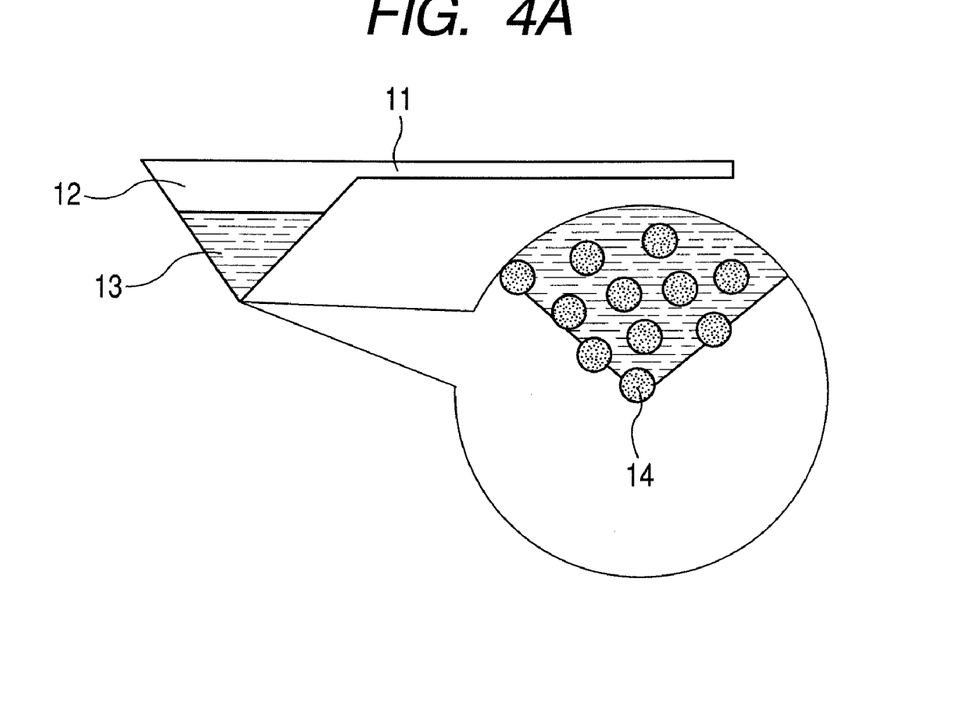
Figure 4B:
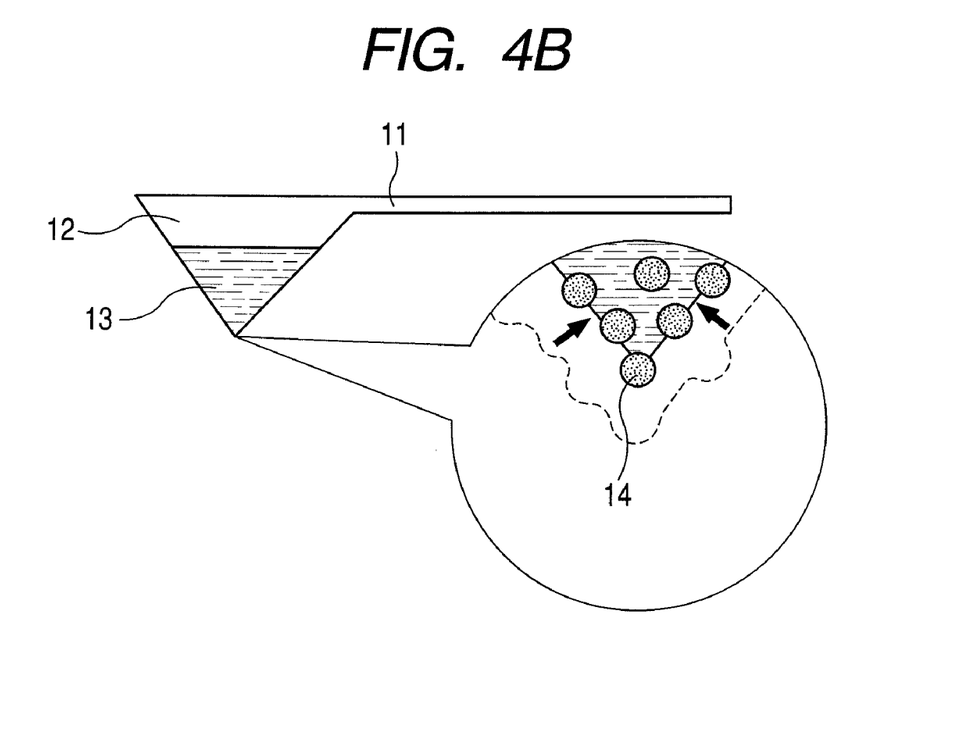

Hereinafter, an example in which vibrational spectroscopic analysis is repeated several times using the same probe will be described (FIGS. 4A and 4B).

In order to perform measurement using a probe for vibrational spectroscopic analysis which has been used for the analysis plural times at the same sensitivity as that of an unused probe, the following is required. That is, it is necessary to remove the molecules of the sample which are adsorbed to the metal fine particles 14 (or the metal fine particles 14 for which the metal film 15 is formed on the surfaces thereof), the metal fine particles 14 (or the metal fine particles 14 for which the metal film 15 is formed on the surfaces thereof), and the surface of the probe 13.

A solution used for etching desirably has such a range of pH level that the sample which has attached to the metal fine particles 14 (or the metal fine particles 14 for which the metal film 15 is formed on the surfaces thereof), the metal fine particles 14 (or the metal fine particles 14 for which the metal film 15 is formed on the surfaces thereof), and the surface of the probe 13 are dissolved. In particular, the solution desirably has an acid of pH 2 to pH 6 or an alkali of pH 10 to pH 14. A desirable solution is a strong acid solution such as a phosphoric acid solution, a sulfuric acid solution, a hydrochloric acid solution and a chromic acid solution, or a strong alkali solution such as a sodium hydroxide solution and ammonia water. However, the present invention is not particularly limited to these types of acid and alkali. A mixture of several types of acid solutions or a mixture of several types of alkali solutions may be used. Etching conditions including a solution temperature, a concentration, and a time can be set as appropriate based on a state of the reused probe for vibrational spectroscopic analysis.

For example, a probe for vibrational spectroscopic analysis (FIG. 4A) after Raman spectroscopic analysis of copper phthalocyanine (CuPc) is immersed in a 1M of NaOH aqueous solution for several minutes. Then, the tip portion of the probe before etching is further reduced in size, so another single Au fine particle 14 or a plurality of other Au fine particles 14 are exposed on the surface of the tip portion (FIG. 4B).

When the probe for spectroscopic analysis to which no particle attaches is subjected to Raman spectroscopic analysis, Raman scattering from a substance other than the material of the probe for spectroscopic analysis is not observed. Subsequently, when a 0.1 mmol/L of a copper phthalocyanine (CuPc) aqueous solution is dropped on the glass substrate and dried and then the probe for spectroscopic analysis is brought into contact with the glass substrate to perform Raman spectroscopic analysis, a surface enhanced Raman scattering intensity becomes substantially equal to the result obtained by the first spectroscopic analysis.

Even when etching is repeated several times, the surface enhanced Raman scattering intensity substantially equal to the result of the first spectroscopic analysis is obtained, so the life of the probe for vibrational spectroscopic analysis can be lengthened.

EXAMPLES

Hereinafter, examples of the present invention will be described. The present invention is not limited to the following Examples.

Example 1

The projected portion 12 of a pyramid structure located at the tip end of the cantilever 11 of a Si material available on the market for use in a scanning probe microscope was placed in a sample chamber of a focused ion beam apparatus having a liquid Ga ion source. The projected portion 12 was placed such that the bottom surface thereof was parallel to an irradiation ion beam. The cross sectional surface of the projected portion 12 was processed or partially etched by controlling the focused ion beam diameter and a probe current (FIG. 2A). After etching, the projected portion 12 had a square planar surface whose each side length was 10 μm.

Subsequently, the metal fine particle layer 22 (40 nm) made of $Au_{0.4}Si_{0.6}$ and the Si layer 23 (30 nm) were alternately layered on the projected portion 12 by a sputtering method. Therefore, the layered film 21 whose film thickness was approximately 1 μm was formed (FIG. 2B).

Subsequently, the cantilever 11 on which the layered film 21 was formed was heated at 250° C. for 30 minutes in an inert gas (Ar) atmosphere at an atmospheric pressure. The morphology of the sample was observed using a field emission scanning electron microscope (FE-SEM). As a result, it was found that a large number of Au fine particles were dispersed in the layered film 21 and a large number of Au fine particles 14 were exposed on the surface of the layered film 21 (FIG. 2C). This is the Au fine particle dispersed film 24. The particle size of the Au fine particles is approximately 10 nm. The Au fine particle dispersed film 24 is processed by focused ion beam etching to form the probe 13 having a pyramid structure.

At this time, the probe 13 had a bottom side length of 10 μm and a height of approximately 10 μm. The tip portion shape of the probe 13 was a hemispherical shape whose radius of curvature was approximately 10 nm. A single Au fine particle 14 whose particle size was 10 nm was located in the tip portion of the probe 13 (right side of each of FIGS. 2D and 1A).

Subsequently, a 0.1 mmol/L copper phthalocyanine (CuPc) aqueous solution was dropped on a glass substrate and dried. Then, the probe 13 was brought into contact with the glass substrate and the tip portion thereof was irradiated with light to perform Raman spectroscopic analysis. As a result, surface enhanced Raman scattered light (SERS) of CuPc was obtained.

In the step of FIG. 2C, another cantilever 11 with an Au fine particle dispersed film 24 was prepared. The prepared Au fine particle dispersed film 24 was processed by focused ion beam etching to form the probe 13 having a pyramid structure. At this time, as in the above-mentioned case, the probe 13 had a bottom side length of 10 μm and a height of approximately 10 μm. The tip portion shape of the probe 13 was a hemispherical shape whose radius of curvature was 20 nm. Unlike the above-mentioned case, three Au fine particles 14 each having a particle size of 10 nm were bonded to one another in the tip portion of the probe 13 (left side of FIG. 1A). The focused ion beam apparatus includes SEM as well, so the positions of the metal fine particles can be checked to form the probe while observing a SEM screen. Therefore, a single metal fine particle or a plurality of metal fine particles can be arbitrarily provided in the tip portion of the probe.

Subsequently, a 0.1 mmol copper phthalocyanine (CuPc) aqueous solution was dropped on a glass substrate and dried. Then, the probe 13 was brought into contact with the glass substrate and the tip portion thereof was irradiated with laser light to perform Raman spectroscopic analysis. As a result, surface enhanced Raman scattered light (SERS) of CuPc was obtained.

When the former case was compared with the latter case, the surface enhanced Raman scattered light intensity of CuPc which was obtained in the later case is increased to approximately 1.5 times the surface enhanced Raman scattered light intensity of CuPc which is obtained in the former case.

According to the present invention, it is possible to control the thin film formation conditions such as the film thickness ratio between the metal fine particle layer 22 and the Si layer 23, the number of layers, and the composition ratio between Au and Si and the heat treatment conditions such as the heat treatment temperature and the heat treatment atmosphere. Therefore, the particle size of the metal fine particles 14 and the dispersibility of the metal fine particles 14 (interspace distance between the metal fine particles 14) can be controlled.

When the number of metal fine particles 14 provided in the tip portion of the probe by etching is controlled, the surface enhanced Raman scattered light intensity can be controlled as desired. That is, when the plurality of metal fine particles 14 which are located in the tip portion of the probe 13 are bonded to each other or brought close to each other, the electromagnetic field intensity increases in a bonding or closely arranged portion between the metal fine particles 14. Therefore, the surface enhanced Raman scattered light can be measured at high sensitivity by taking advantage of the phenomenon.

Example 2

This example shows an example in which the metal fine particles 14 were covered with the metal film 15.

The probe 13 illustrated in FIG. 3A was produced by the same method as Example 1 (FIGS. 2A to 2D).

At this time, the probe 13 had a bottom side length of 10 μm and a height of approximately 10 μm. The tip portion shape of the probe 13 was a hemispherical shape whose radius of curvature was approximately 20 nm. Three Au fine particles 14 each having a particle size of 10 nm were close to one another in the tip portion of the probe 13 and the interspace distance between the respective Au fine particles 14 was approximately 5 nm (left side of FIG. 1A).

Subsequently, the metal film 15 is formed by plating on the surfaces of the Au fine particles 14 exposed on the tip portion of the probe 13. For example, the case where electrolytic Ag plating is employed will be described.

A Pt substrate is used as an anode. The Pt substrate and the cantilever 11 with the probe 13 were placed in SILVREX50 (produced by Electroplating Engineers of Japan, Ltd.) maintained at 55° C. by heating. A current of 1 $A/dm^2$ was applied between the electrodes for 10 seconds. The sample was observed using the FE-SEM. As a result, the Ag film 15 having a film thickness of approximately 2 nm was formed on the surfaces of the Au fine particles 14 exposed on the tip portion of the probe 13. The interspace distance between the respective Au fine particles 14 was reduced to approximately 1 nm.

A 0.1 mmol/L copper phthalocyanine (CuPc) aqueous solution was dropped on a glass substrate and dried. Then, the probe 13 was brought into contact with the glass substrate and the tip portion of the probe 13 was irradiated with laser light to perform Raman spectroscopic analysis. As a result, the surface enhanced Raman scattered light of CuPc was obtained. The obtained surface enhanced Raman scattered light intensity was increased to approximately two times the surface enhanced Raman scattered light intensity in Example 1.

The following is apparent from the above-mentioned result. That is, the Ag film 15 was further formed on the surfaces of the Au fine particles 14 exposed on the tip portion of the probe 13, so the electromagnetic field intensity increased in the interspace between the metal fine particles 14 with the metal film 15 to improve analysis sensitivity. Therefore, it was possible to measure the surface enhanced Raman scattered light intensity at higher sensitivity.

Metals such as Au, Pd, or Pt instead of Ag can be used for the metal film 15. An organic substance which includes a functional group such as a thiol group or an amino group and has surface enhanced Raman activity can be used as a measurement sample other than CuPc described above.

Example 3

In this example, an example will be described in which Raman spectroscopic analysis was performed several times using a probe for vibrational spectroscopic analysis with which Raman spectroscopic analysis has once been performed (FIGS. 4A and 4B).

The probe for vibrational spectroscopic analysis after the Raman spectroscopic analysis was performed in Example 1 was subjected to ultrasonic cleaning with acetone. When the tip portion of the probe 13 was irradiated with laser light again to perform Raman spectroscopic analysis. Then, although cleaning was completed, the surface enhanced Raman scattering of CuPc was observed. Therefore, it was found that a slight amount of CuPc molecules attaches to the tip portion of the probe 13.

Then, the tip portion of the probe was immersed for etching in a 1M NaOH aqueous solution for several minutes. The morphology of the tip portion of the probe was observed using the FE-SEM. As a result, it was found that the tip portion of the probe 13 was further reduced in size and the Au fine particles 14 dispersed in the tip portion of the probe 13 were newly exposed (FIG. 4B). The tip portion of the probe for spectroscopic analysis was subjected to Raman spectroscopic analysis again. As a result, the SERS of CuPc was not observed.

Subsequently, a 0.1 mmol/L copper phthalocyanine (CuPc) aqueous solution was dropped on a glass substrate and dried. Then, the tip portion of the probe was brought into contact with the glass substrate again to perform Raman spectroscopic analysis. As a result, the SERS of CuPc was obtained and the same Raman scattered light intensity as in Example 1 was obtained.

As is apparent from this result, the metal fine particles 14 dispersed in the probe were newly exposed instead of the previously exposed metal fine particles 14 which were removed by etching. Therefore, it was found that, even when subsequent etching was repeated, the scattered light intensity equal to the surface enhanced Raman scattered light intensity obtained by the first spectroscopic analysis was obtained and thus it was possible to lengthen the life of the probe for vibrational spectroscopic analysis. The above description can be also applied to Example 2.

While the present invention has been described with reference to exemplary Examples, it is to be understood that the invention is not limited to the disclosed exemplary Examples. The scope of the following claims is to be accorded the broadest interpretation so as to encompass all such modifications and equivalent structures and functions.

This application claims the benefit of Japanese Patent Application No. 2007-128271, filed May 14, 2007, which is hereby incorporated by reference herein in its entirety.

What is claimed is:

1. A probe for use in surface enhanced vibrational spectroscopic analysis, the probe being formed on a cantilever, the probe comprising a plurality of metal fine particles dispersed therein, the plurality of the metal fine particles being exposed on a surface of the probe.

2. A probe according to claim 1, wherein the exposed metal fine particles have an exposed portion covered with a metal film.

3. A probe according to claim 1, wherein
the probe comprises a Si material.

4. A probe according to claim 1, wherein the metal fine particles have a particle size of 1 nm to 30 nm and have an interspace distance therebetween of 0 nm to 100 nm.

5. A probe according to claim 1, wherein the metal fine particles are comprised of a material selected from the group consisting of Au, Ag, Pd and Pt.

6. A probe according to claim 2, wherein the metal film is comprised of a material selected from the group consisting of Au, Ag, Pd and Pt.

7. A probe according to claim 2, wherein
the metal film has a film thickness of 1 nm to 50 nm.

8. A method of manufacturing a probe for use in surface enhanced vibrational spectroscopic analysis, comprising:
   forming a projected portion on a cantilever;
   forming a Si film including a metal fine particle layer so as to be in contact with the projected portion;
   heating the Si film including the metal fine particle layer to disperse metal fine particles in the Si film; and
   forming the probe by processing the Si film,
   wherein a plurality of the metal fine particles are exposed on a surface of the probe by the step of forming the probe.

9. A method according to claim 8, wherein the step of forming the probe comprises etching.

10. A method according to claim 9, wherein the number of the metal fine particles provided in a tip portion of the probe is controlled by the etching.

11. A method according to claim 8, further comprising a step of forming a metal film so as to cover the exposed metal fine particles after the step of forming the probe.

12. A method according to claim 11, wherein the step of forming the metal film comprises plating.

* * * * *